US00PP35145P2

(12) United States Plant Patent
Bourne

(10) Patent No.: US PP35,145 P2
(45) Date of Patent: May 2, 2023

(54) GRAPEVINE NAMED 'SV34-136-114'

(50) Latin Name: *Vitis vinifera*
Varietal Denomination: SV34-136-114

(71) Applicant: Sunview Vineyards of California, Inc., Delano, CA (US)

(72) Inventor: Timothy F Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 17/803,351

(22) Filed: May 26, 2022

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205
CPC ... A01H 5/08; A01H 5/02; A01H 5/00; A01H 6/88
See application file for complete search history.

*Primary Examiner* — June Hwu
(74) *Attorney, Agent, or Firm* — Eric C. Cole; Baker Manock & Jensen. PC

(57) ABSTRACT

A new and distinct variety of grapevine named 'SV34-136-114' particularly characterized by its very large, crisp dark red colored berries that have a light muscat flavor and which ripen in mid-September in the McFarland, Calif. area.

4 Drawing Sheets scientific name of the genus and species of the plant claimed: The plant claimed relates to a new and distinct variety of *Vitis vinifera*.

Variety denomination: The plant claimed shall be known as 'SV34-136-114'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV34-136-114'. As used herein, 'grapevine' refers to all plant parts including, vines, canes, tendrils, leaves, fruit and roots of 'SV34-136-114'. Grapevine named 'SV34-136-114' is the result of an effort to produce a late season grape with non-astringent fruit characteristics. This new grapevine originated from a cross conducted in May 2013 near McFarland, Calif. between female grapevine plant selection 'SV18-9-1' (unpatented) and male grapevine plant 'Autumn King' (U.S. Plant Pat. No. 16,284). Resultant ovules from the cross were harvested 42 days after pollination and cultured on 'McCown's Woody Plant Medium'. Subsequently, the resultant embryonic plants were cultured in the same medium in the laboratory under twelve hours of light from standard fluorescent lamps at 29° C. The seedlings from this effort were transplanted to the greenhouse in November of 2001 and grown in the greenhouse at 29° C. with 12 hours illumination under high pressure sodium vapor lamps. The seedling population of 123 plants was planted in the field in the spring of 2014 near McFarland, Calif. The new grapevine was selected from this seedling population on Aug. 25, 2016. It was then propagated by cuttings and grafted to 'Freedom' (unpatented) rootstock near McFarland, Calif. in 2017. The present invention has been found to retain its distinctive characteristics through two successive asexual propagations.

Grapevine named 'SV34-136-114' differs from its female parent grapevine 'SV18-9-1' (unpatented) in that grapevine named 'SV34-136-114' has very large, elliptic, seedless berries and flowers with functional pollen, whereas 'SV18-9-1' (unpatented) has small, elliptic berries and flowers that are pistillate.

Grapevine named 'SV34-136-114' differs from its male parent, commercial cultivar 'Autumn King' (U.S. Plant Pat. No. 16,284) in that grapevine named 'SV34-136-114' has red berries while 'Autumn King' (U.S. Plant Pat. No. 16,284) has green berries.

Grapevine named 'SV34-136-114' differs from the commercial cultivar 'Scarlet Royal' (U.S. Plant Pat. No. 16,229) in that grapevine named 'SV34-136-114' has berries which are elliptic and which develop lobes with gibberellic acid application (see FIG. 3, fruit clusters treated with gibberellic acid and trunk girdling at right of figure) while 'Scarlet Royal' (U.S. Plant Pat. No. 16,229) has berries which are narrow elliptic in shape and do not develop lobes following gibberellic acid application. Additionally, fruit of grapevine named 'SV34-136-114' has a slight muscat flavor with no astringency while fruit of 'Scarlet Royal' (U.S. Plant Pat. No. 16,229) has a typical *Vitis vinifera* neutral flavor and is astringent at full maturity

SUMMARY OF THE INVENTION

The following are the most outstanding and distinguishing characteristics of this new variety when grown under normal horticultural practices near McFarland, Calif.:

1. Dark red berries;
2. Crisp berry texture; and
3. Very large, sweet, unusual shaped berries.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The photographs were taken from the seedling vine and from a plant about 4 years-old, grown in a field near McFarland, Calif. in 2021.

DETAILED BOTANICAL DESCRIPTION

Figure 1:
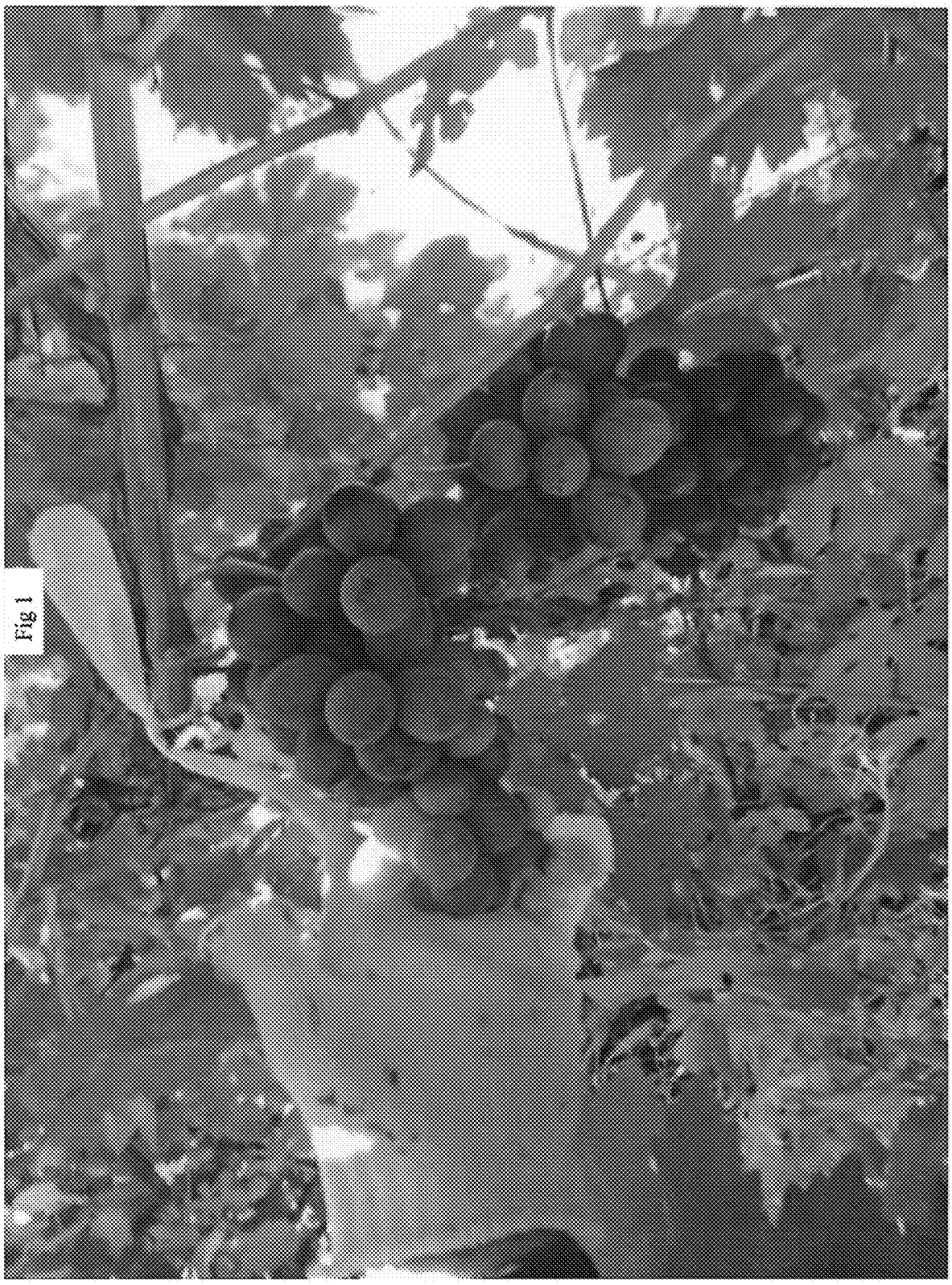
FIG. 1 Natural, untreated fruit clusters on the seedling vine.
Figure 2:
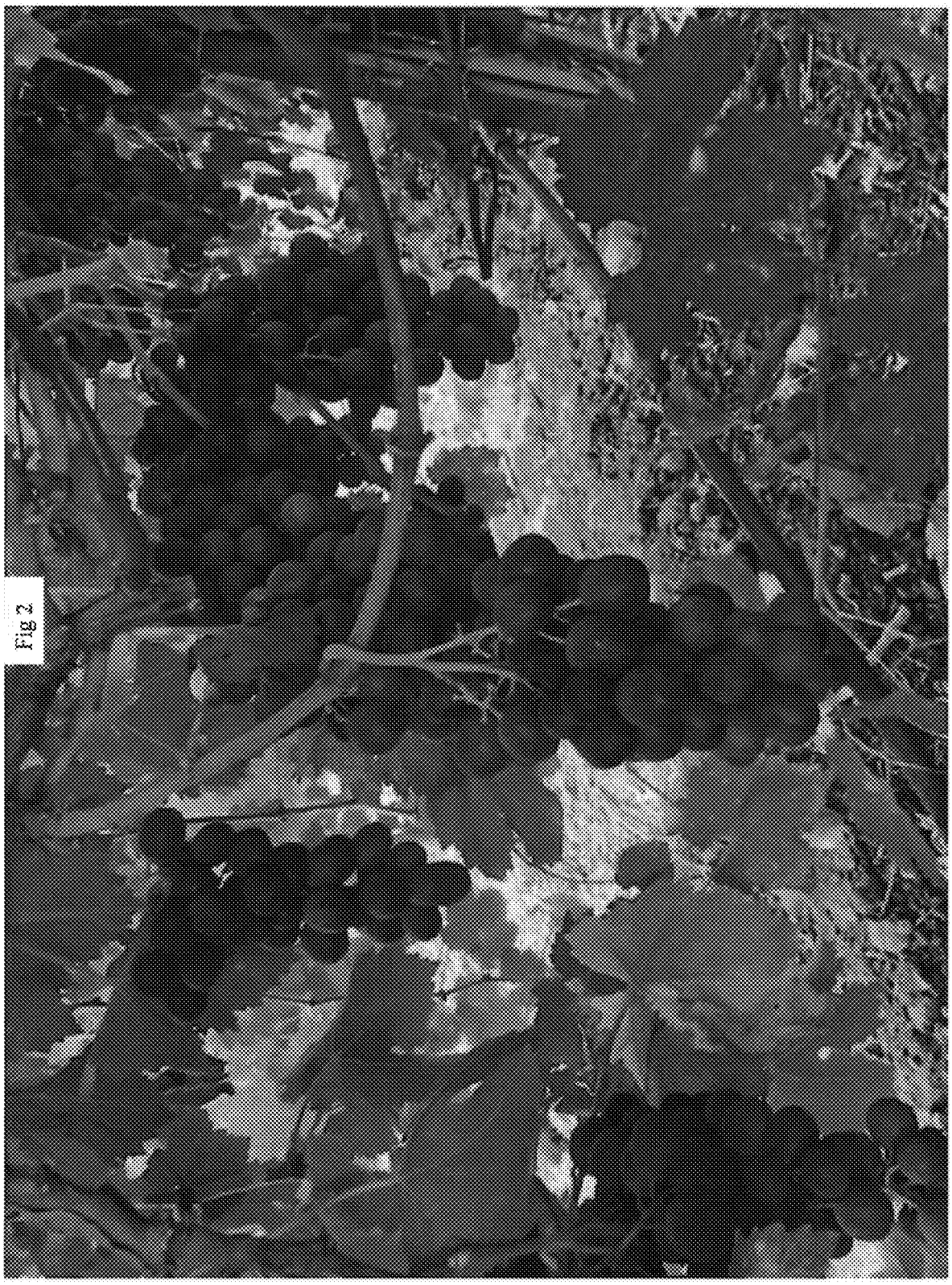
FIG. 2 Vine with fruit clusters treated with exogenous gibberellic acid and trunk girdling.
Figure 3:
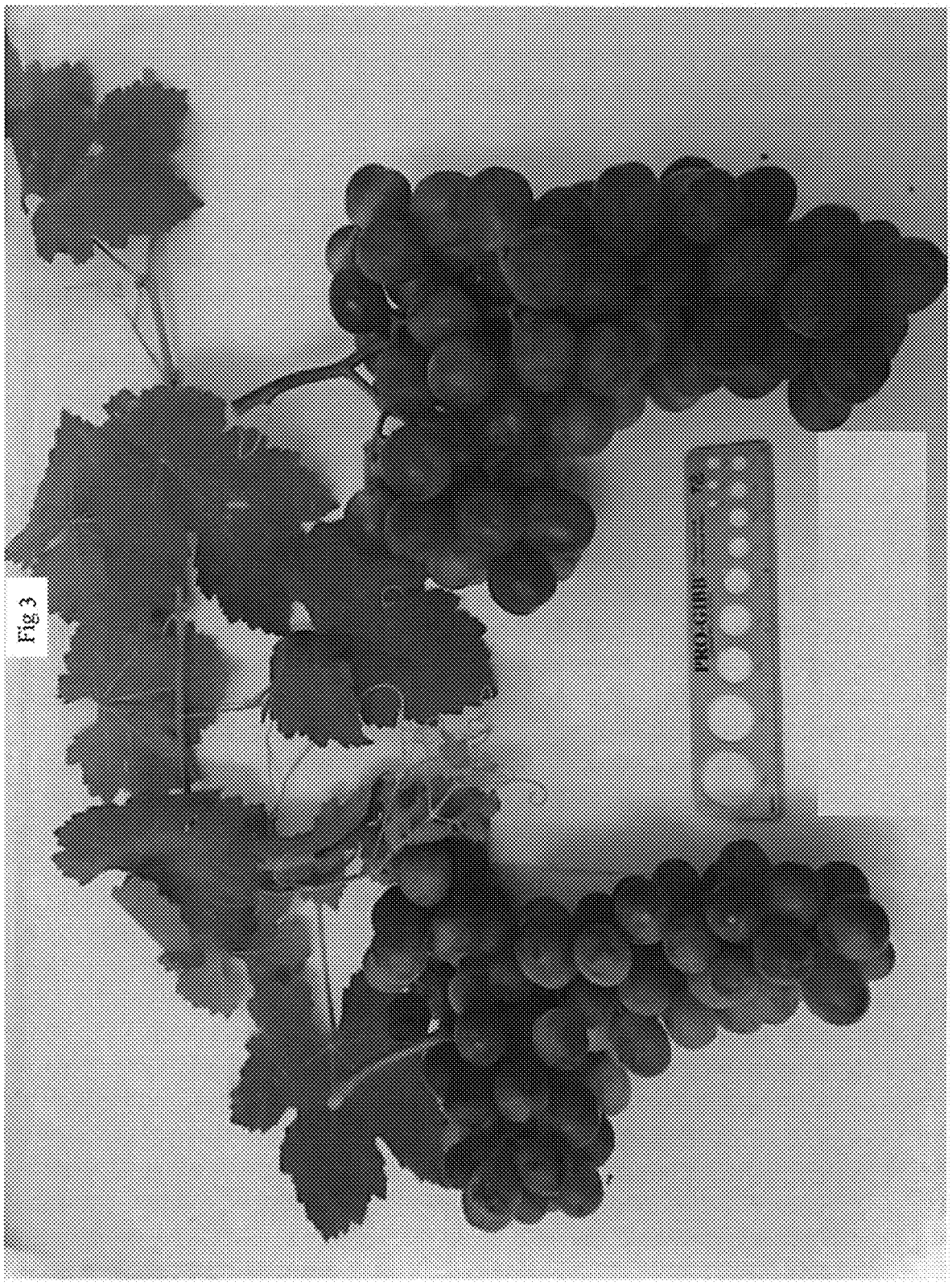
FIG. 3 Shoots, leaves, and tendrils with natural fruit cluster at left and fruit clusters treated with gibberellic acid and trunk girdling at right.
Figure 4:
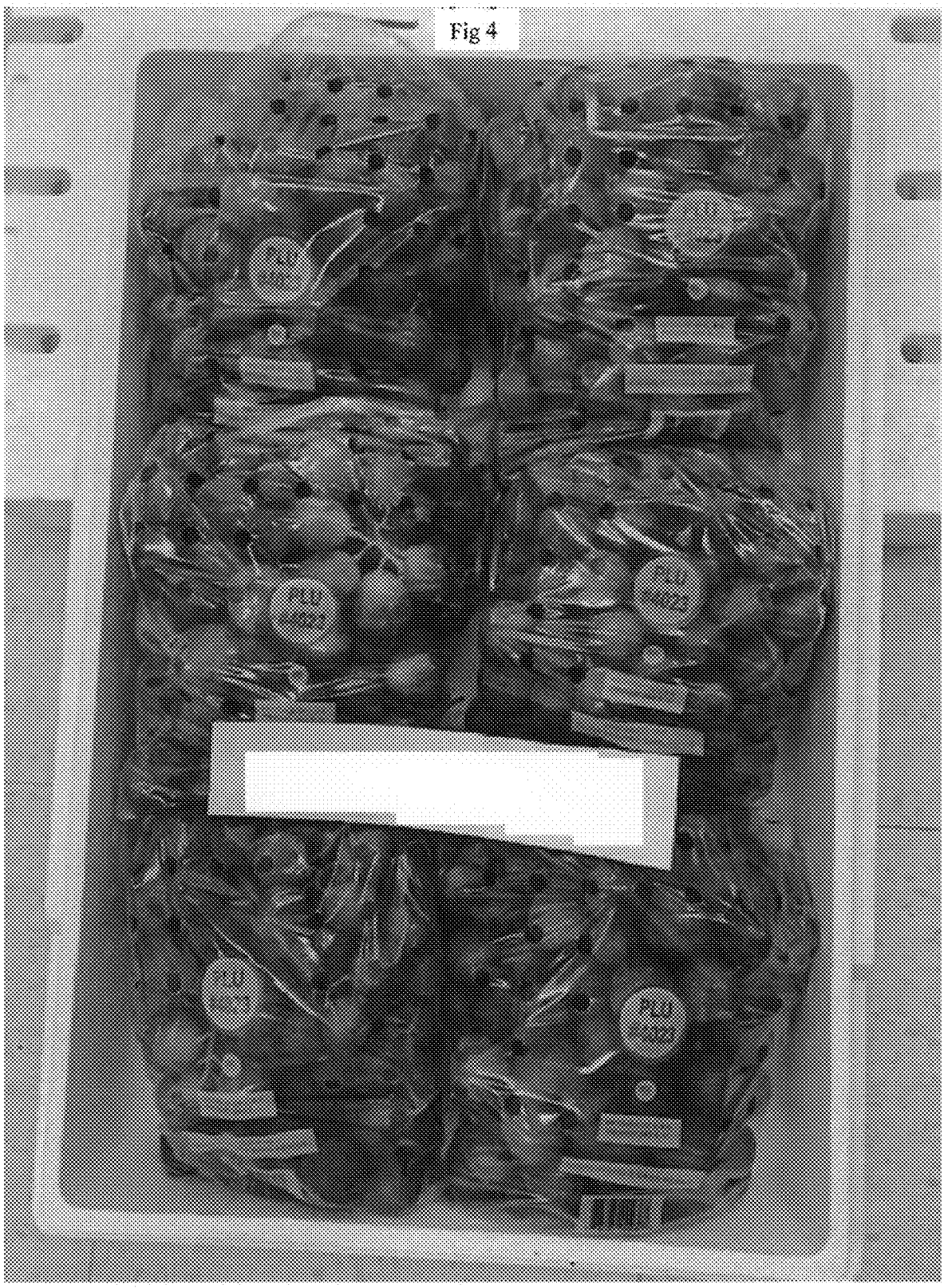
FIG. 4 Fruit clusters packaged for storage and shipping evaluation.

The following detailed description sets forth the distinctive characteristics of grapevine named 'SV34-136-114'. Descriptions of the new invention apply to vines of 'SV34-136-114' grown on 'Freedom' (unpatented) rootstock at a density of 1,537 vines per hectare grown near McFarland, Calif. in 2021. These vines were in their fourth year of production, having been planted in 2017. These descriptions are believed to apply generally to the new variety grown under similar circumstances elsewhere. Color references are to The Royal Horticultural Society's Colour Chart, The Royal Horticultural Society, London, United Kingdom, 1966, 1986, 1995, 2001. Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis* spp.) (Anonymous, International Plant Genetic Resources Institute, 1997, ISBN 92-9043-352-3).

Classification:

*Family*.—Vitaceae.

*Botanical name*.—*Vitis vinifera*.

*Variety name*.—'SV34-136-114'.

Plant:

*Vigor*.—Very vigorous. Vines spur-pruned and shoot thinned to 32 shoots average 413 cm of growth per cane.

*Density of foliage*.—Moderate.

*Productivity*.—Very productive when spur pruned, up to 32,816 kg/hectare.

*Hardiness*.—Hardiness observed to 0° C.

*Rootstock*.—'Freedom' (unpatented).

Trunk:

*Shape*.—Broadly elliptic.

*Straps*.—Long, split.

*Surface texture*.—Shaggy.

*Trunk circumference*.—22.4 cm at 1.0 m of height.

*Inner bark color*.—RHS Greyed Orange group 172B.

*Outer bark color*.—RHS Brown group N200B.

Mature leaves:

*Average blade length*.—13.6 cm.

*Average blade width*.—19.1 cm.

*Size of blade*.—Large.

*Shape*.—Pentagonal.

*Number of lobes*.—5.

*Anthocyanin coloration of main veins on the upper side of the blade*.—Present, weak to medium.

*Mature leaf profile*.—Cupped upwards around entire margin.

*Blistering* (*upper surface*).—Absent.

*Leaf blade tip*.—Curved downward.

*Margins*.—Lobed, serrated, undulating.

*Apex*.—Broadly acuminate.

*Bases*.—Sagittate.

*Thickness*.—Medium.

*Undulation of blade between main and lateral veins*.—Slight.

*Shape of teeth*.—Broadly conical, both sides convex.

*Length of teeth*.—About 7 mm.

*Width of teeth*.—About 11 mm.

*Ratio length/width of teeth*.—7:11.

*General shape of petiole sinus*.—Slightly open.

*Tooth at petiole sinus*.—Absent.

*Petiole sinus limited by veins*.—Absent.

*Shape of upper lateral sinus*.—Open.

*Prostrate hairs between veins* (*lower surface*).—Sparse.

*Erect hairs between veins* (*lower surface*).—Absent.

*Prostrate hairs on main veins* (*lower surface*).—Very sparse.

*Density of erect hairs on main veins* (*lower surface*).—Sparse.

*Prostrate hairs on main veins* (*upper surface*).—Sparse.

*Erect hairs on main veins* (*upper surface*).—Very sparse.

*Upper surface*.—Summer color: RHS Yellow Green group 147A. Surface texture: Smooth. Surface appearance: Dull. Goffering of blade: Absent.

*Lower surface*.—Summer color: RHS Yellow Green group 147B. Anthocyanin coloration of main veins on lower leaf surface: Absent. Glossiness: Low. Pubescence distal portion of surface: Absent. Surface texture: Rough. Surface appearance: Dull.

*Petiole*.—Length: 9.3 cm. Length of petiole compared to middle vein: Much shorter. Density of prostrate hairs: Very sparse. Density of erect hairs: Medium. Shape of base of petiole sinus: Half open. Color: In shade: RHS Yellow Green group 144C. In sun: RHS Yellow Green group 144B.

Tendrils:

*Number*.—Bifurcated and trifurcated; forming irregularly above node 4.

*Length*.—20.6 cm.

*Diameter*.—2.3 mm.

*Texture*.—Smooth.

*Color*.—RHS Yellow Green group 144B.

Growing tips (young shoot):

*Pubescence*.—Abundant, prostrate.

*Color*.—RHS Yellow Green group 144C.

*Anthocyanins*.—Absent.

*Shape*.—Rounded.

*Apex*.—Fully open.

*Shoot attitude*.—Erect.

Green summer shoots:

*Internode color upper surface*.—RHS Yellow Green group 144A.

*Internode color lower surface*.—RHS Yellow Green group 144B.

*Node color upper surface*.—RHS Yellow Green group 144C.

*Node color lower surface*.—RHS Yellow Green group 144B.

*Density of erect hairs on internodes*.—Absent.

Woody shoot:

*Canes*.—Shape: Elliptic. Internode length: 10.1 cm. Width at node: 14.8 mm. Surface: Smooth. Main color: Greyed Orange group 175C. Lenticels: Inconspicuous.

*Buds*.—Shape: Pointed. Cane bud fruitfulness: Highly fruitful from basal buds, each shoot producing one or two flower clusters. Length: 6.2 mm. Width: 5.8 mm. Height: 5.2 mm. Color: Greyed orange group 174A. Bud burst: Medium, Mar. 11, 2022.

Flowers:

*Flower sex*.—Perfect.

*Position of first flowering nodes*.—2nd, 3rd or 4th node.

*Number of inflorescences per shoot*.—2.

*Calyptra color*.—Yellow green group 146C.

*Ovary length*.—2 mm.

*Ovary width*.—1.5 mm.

*Ovary color*.—Green group 141B.

*Filament length*.—2 mm.

*Filament color*.—Translucent, absence of pigmentation.

*Anther length*.—1 mm.

*Anther color*.—Yellow group 8C.

*Date of full bloom*.—May 10, 2022.

Fruit:

*Ripening period*.—Late mid-season, McFarland, Calif.

*Date of ripening*.—Sep. 13, 2021 McFarland, Calif.

*Use*.—Fresh market.

*Keeping quality*.—Very good.

*Shipping quality*.—Good.

*Date of first harvest*.—Sep. 13, 2021.

*Solids-sugar*.—High.

*Refractometer test*.—20 brix.

*Titratable acidity*.—0.33 g/liter.

*Juice*.—pH=4.3.

*Bunch*.—Size: Large. Length (peduncle excluded): About 21.5 cm. Width: About 13.2 cm. Weight: Natural, without gibberellic acid treatment: 535 g. With gibberellic acid treatment: 667.5 g. Density: Loose, well filled. Number of berries in untreated clusters: 70. Number of berries in clusters treated with gibberellic acid: 64. Form: Conical.

*Peduncle*.—Length: About 4.8 cm. Lignification: 2 cm of peduncle. Color: RHS Yellow Green group 144B.

*Berry*.—Size: Large. Uniformity of size: Uniform. Weight Natural, without gibberellic acid treatment: 7.5 g. With gibberellic acid treatment: 10.3 g. Shape: Natural, without gibberellic acid treatment: Elliptic. With gibberellic acid treatment: Elliptic to spherical, with some lobes developing. Presence of seeds: Seedless; most berries develop one or two small, partially lignified rudimentary seeds less than 1.0 mm in length. Cross section: Circular. Dimensions (natural, untreated clusters): Longitudinal axis: 2.5 cm at base. Horizontal axis: About 2.2 cm. Dimensions (clusters treated with gibberellic acid): Longitudinal axis: 2.6 cm. Horizontal axis: 2.5 cm. Skin color (without bloom): RHS Red Purple group 59A to Purple group N77A. Coloration of flesh: Translucent, absence of anthocyanin pigmentation. Juiciness of flesh: Very juicy. Berry firmness: Very firm. Particular flavor: Light muscat. Bloom (cuticular wax): Heavy. Pedicel length: 1.0 cm. Berry separation from pedicel: With difficulty.

*Skin*.—Thickness: Medium. Texture: Crisp. Reticulation: Absent. Roughness: Absent. Tenacity: Tenacious to flesh. Tendency to crack: Resistant.

Disease and insect resistance: No particular resistance or susceptibility has been observed. Normal disease control practices can be used.

Having thus described and illustrated our new variety of grapevine, we claim:

1. A new and distinct variety of grapevine plant named 'SV34-136-114', substantially as illustrated and described herein.

* * * * *